United States Patent [19]
Cosme

[11] Patent Number: 6,077,253
[45] Date of Patent: Jun. 20, 2000

[54] SAFETY NEEDLE ASSEMBLY

[76] Inventor: Edgar Z. Cosme, 1360 N. Lighthouse, Anaheim, Calif. 92801

[21] Appl. No.: 09/441,171

[22] Filed: Nov. 15, 1999

[51] Int. Cl.[7] ..................................................... A61M 5/00
[52] U.S. Cl. .......................... 604/263; 604/192; 128/919
[58] Field of Search .................................... 604/263, 198, 604/192, 187, 110; 128/919

[56] References Cited

U.S. PATENT DOCUMENTS

| | | | |
|---|---|---|---|
| 5,445,619 | 8/1995 | Burns | 604/263 X |
| 5,733,265 | 3/1998 | Bachman et al. | 604/263 |
| 5,735,827 | 4/1998 | Adwers et al. | 604/263 |
| 5,746,726 | 5/1998 | Sweeney et al. | 604/263 |
| 5,749,856 | 5/1998 | Zadini et al. | 604/192 X |

*Primary Examiner*—John Yasko
*Attorney, Agent, or Firm*—Maria Erlinda C. Sarno

[57] ABSTRACT

The present invention relates to a needle shield assembly attachable to a syringe body or other fluid delivery system to protect a user from accidental and unintentional puncture. The safety needle assembly is commonly mounted to a syringe body, preferably by a luer lock adapter, or to other fluid delivery devices used in the medical field. The present invention resides in the use of a retractable tube lock that dictates the covering and uncovering of the sharp tip of a needle or a blunt tip of a cannula by communicating with a stationary hollow tube which houses a retractable hollow tube that axially slips in and out of the stationary tube.

18 Claims, 9 Drawing Sheets

SAFETY NEEDLE ASSEMBLY

BACKGROUND

The present invention relates to a needle shield assembly attachable to a syringe body or other fluid delivery system to protect a user from accidental and unintentional puncture. Public concern has increased to protect a user from coming into physical contact with a used needle due to well documented cases of illness and death brought about by accidental puncture or pricking with contaminated needles. These are usually brought about by direct contact with discarded uncovered contaminated needles or in the capping and uncapping of contaminated needles marketed with friction fitted needle caps. Various designs for shielding the needle have been proposed. These designs, however, are complex even with or without the use of a spring mechanism.

It is therefore an object of the invention to provide a needle assembly having a cover that can shield and unshield the sharp tip of a needle without the need of direct manual manipulation of the needle cover.

It is also an object of the invention to provide a needle assembly that can be operated with one hand.

It is another object of the present invention to provide a needle assembly that is simple in design and easy to operate.

SUMMARY OF THE INVENTION

The invention provides a safety needle assembly having a retractable needle shield for covering and uncovering the tip of a needle. The needle of this invention is attached to a needle hub that is engageable to a syringe body or other fluid delivery systems.

The needle assembly engageable to a fluid delivery device, comprises a hub holding a needle, the hub having a hollow interior for communicating a central lumen of the needle or cannula with the fluid delivery device; a retractable tube lock attachable to the hub, the retractable tube lock having a distal locking projection on an actuating latch communicating with an opening of a stationary tube, the stationary tube having a hollow interior housing a retractable hollow tube, the retractable hollow tube axially movable from an extended position to cover the needle, to a retracted position to expose the needle, the movement controlled by engagement and disengagement of the distal locking projection of the retractable tube lock with the retractable hollow tube.

DETAILED DESCRIPTION OF THE INVENTION

Figure 1:
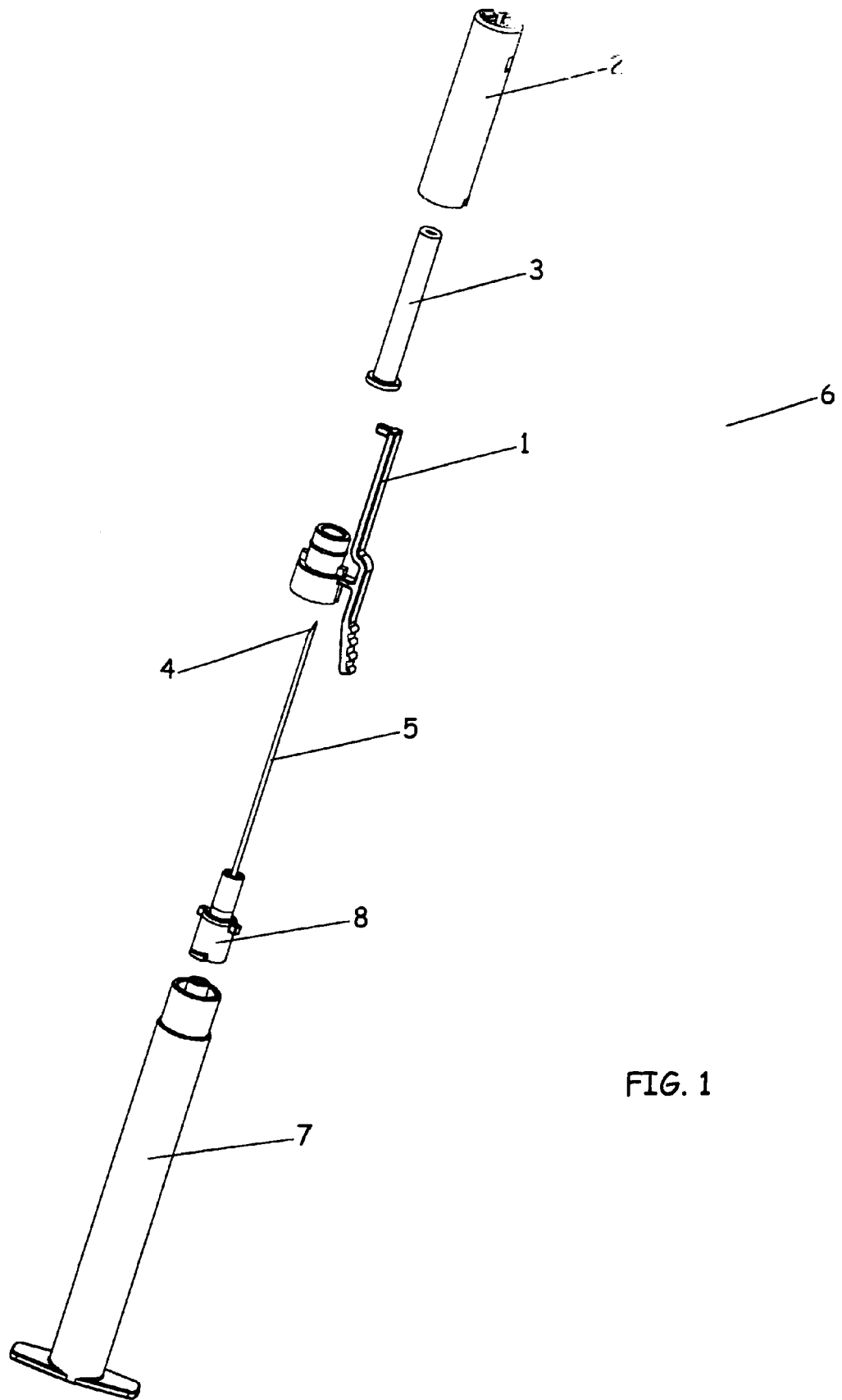
FIG. 1 shows a perspective view of the unassembled parts of a needle assembly with a syringe body.

The present invention resides in the use of a retractable tube lock 1 communicating with a stationary hollow tube 2 which houses a retractable hollow tube 3 that covers and uncovers a sharp tip 4 of a needle 5 or a blunt tip of a cannula. Hereinafter, application and referral to a needle applies equally well to a cannula.

The safety needle assembly 6 is commonly mounted to a syringe body 7, preferably by a luer lock adapter, or to other fluid delivery devices used in the biological and medical field. In this invention, the distal end is the point away from the user while the proximal end is the point close to the user during the operation of the needle assembly. The outer surface of the needle assembly 6 is preferably cylindrical but other geometric shapes such as rectangular and ovoid can be adopted.

Figure 2:
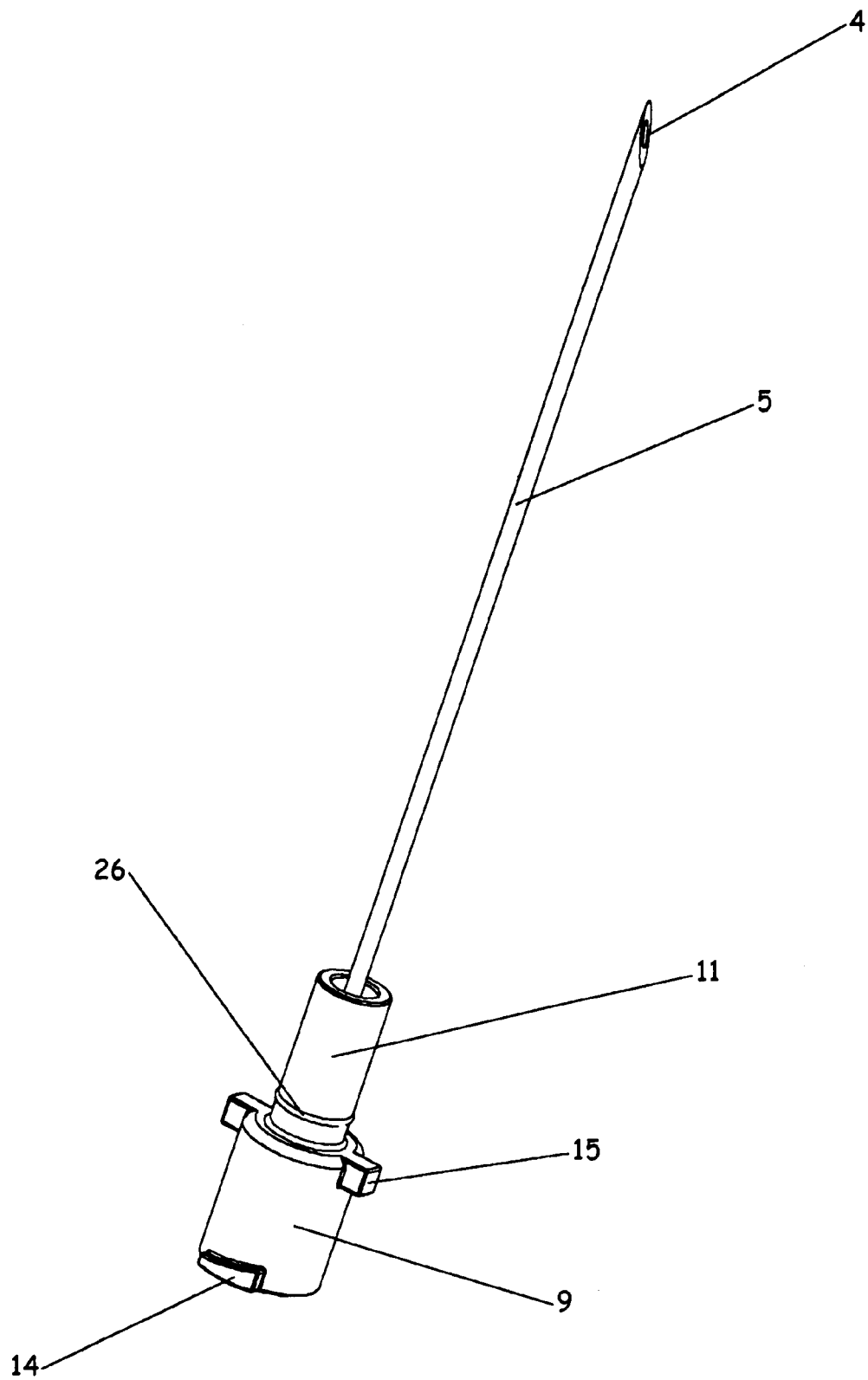
FIG. 2 is a perspective view of a needle hub attached to a sharp tipped needle.
Figure 2A:
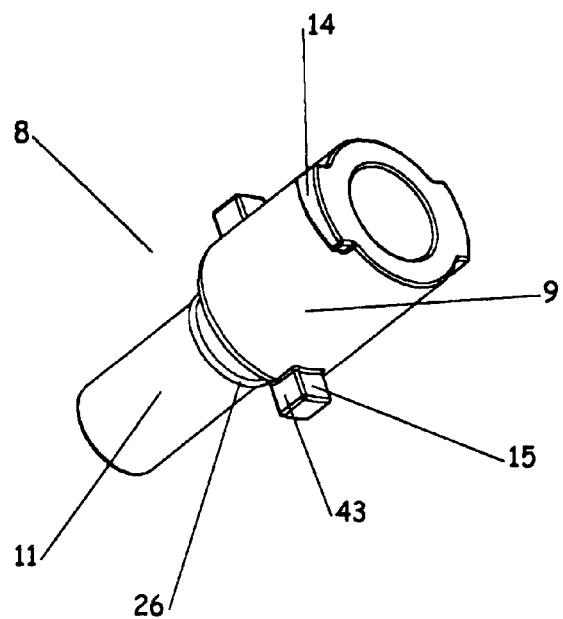
FIG. 2A is a perspective view of the needle hub without a needle.
Figure 2B:
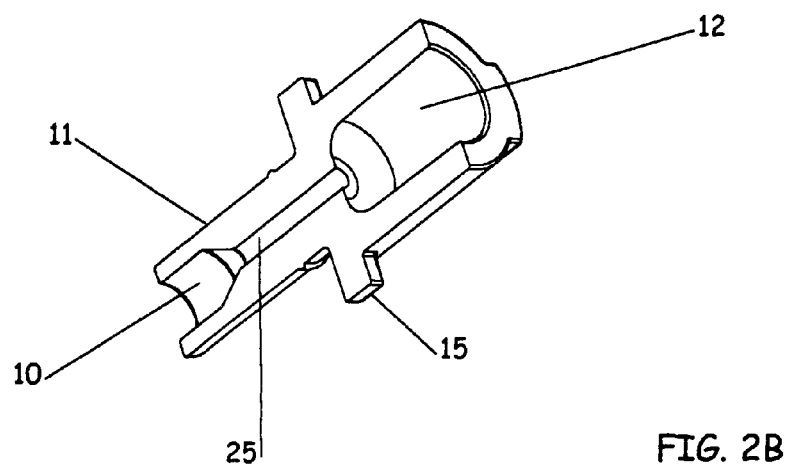
FIG. 2B is a cross sectional view of a needle hub taken along A—A.
Figure 6:
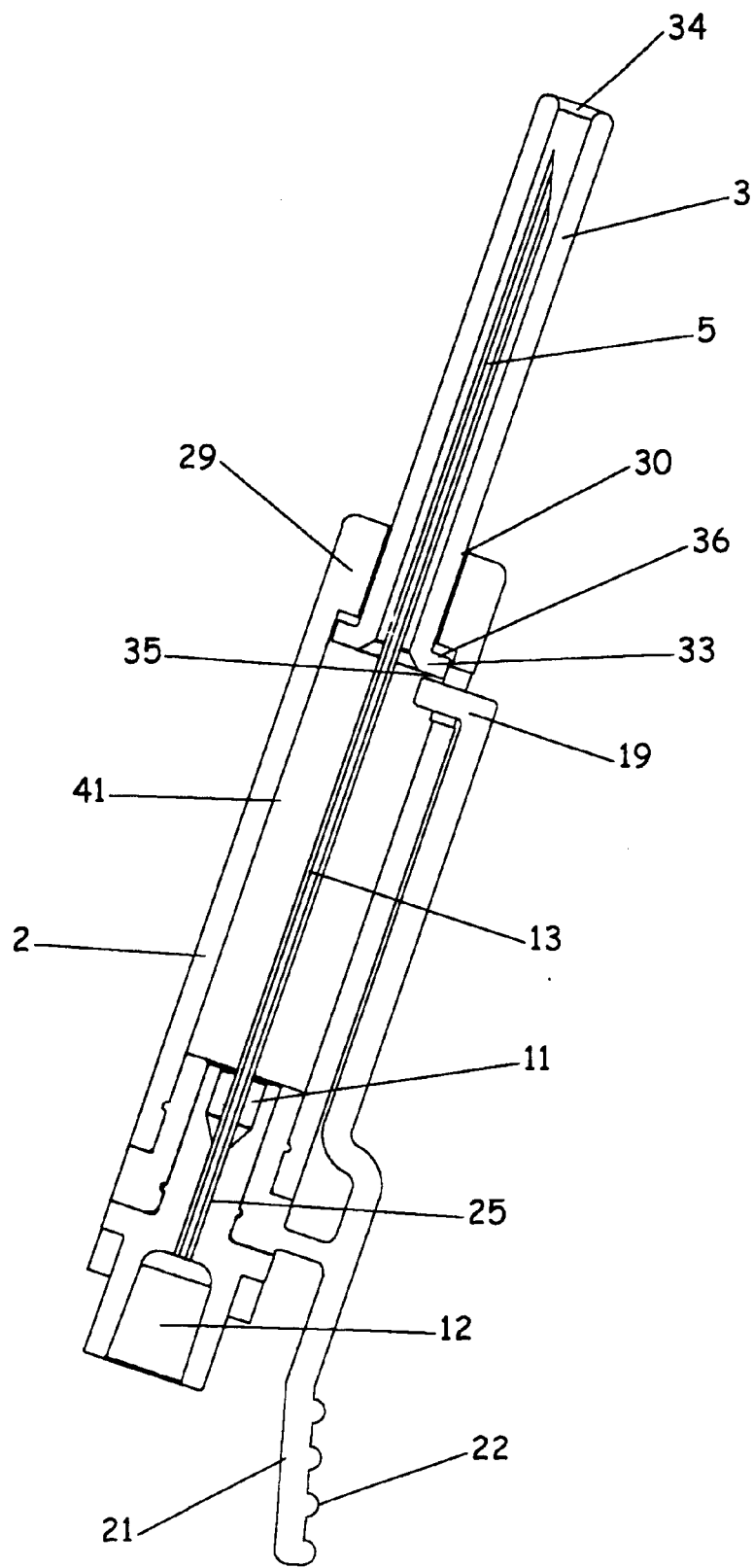
FIG. 6 is a cross sectional view of the needle assembly with the retractable hollow tube covering the needle.
Figure 6A:
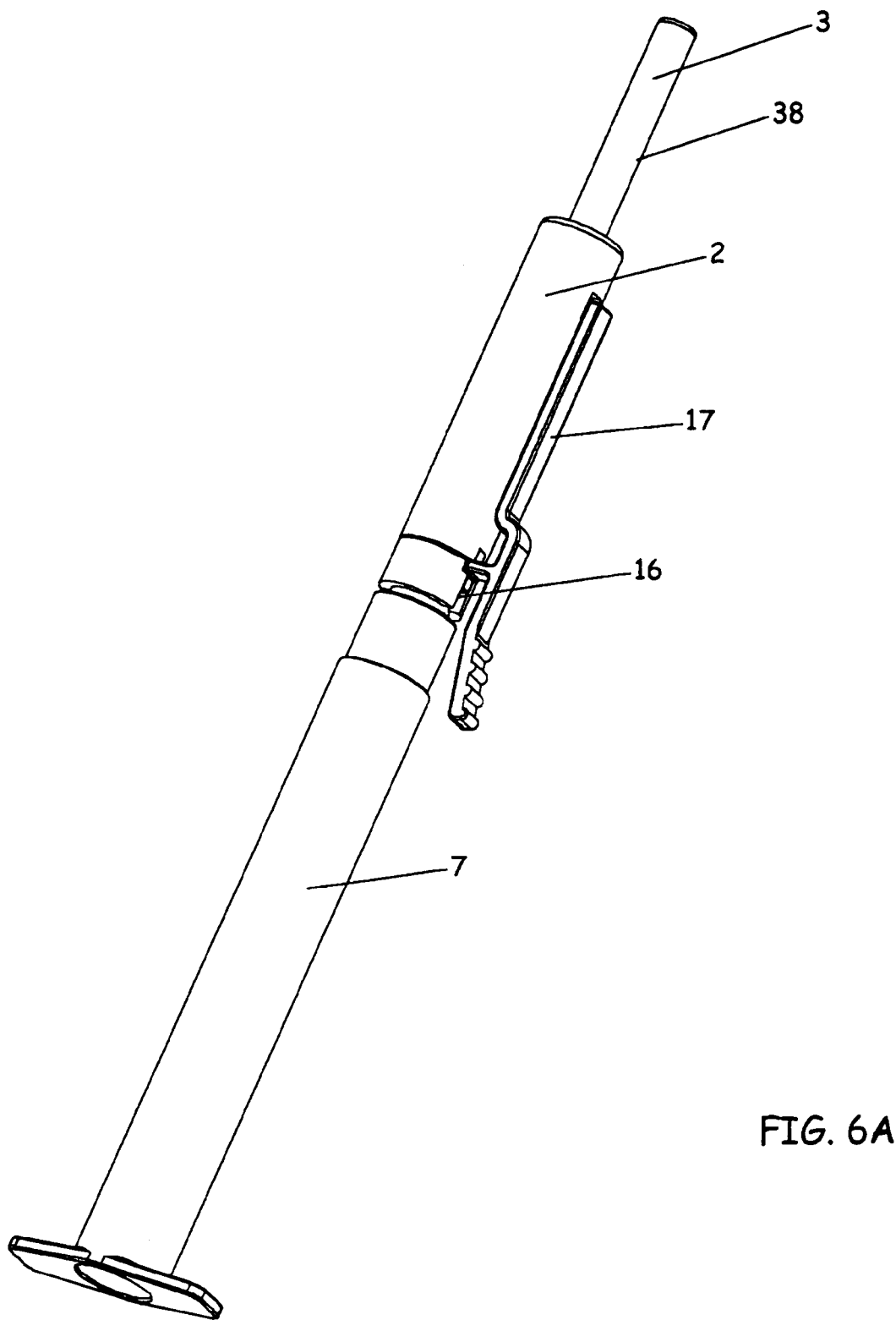
FIG. 6A is a perspective view of the needle assembly attached to a syringe body.
Figure 6B:
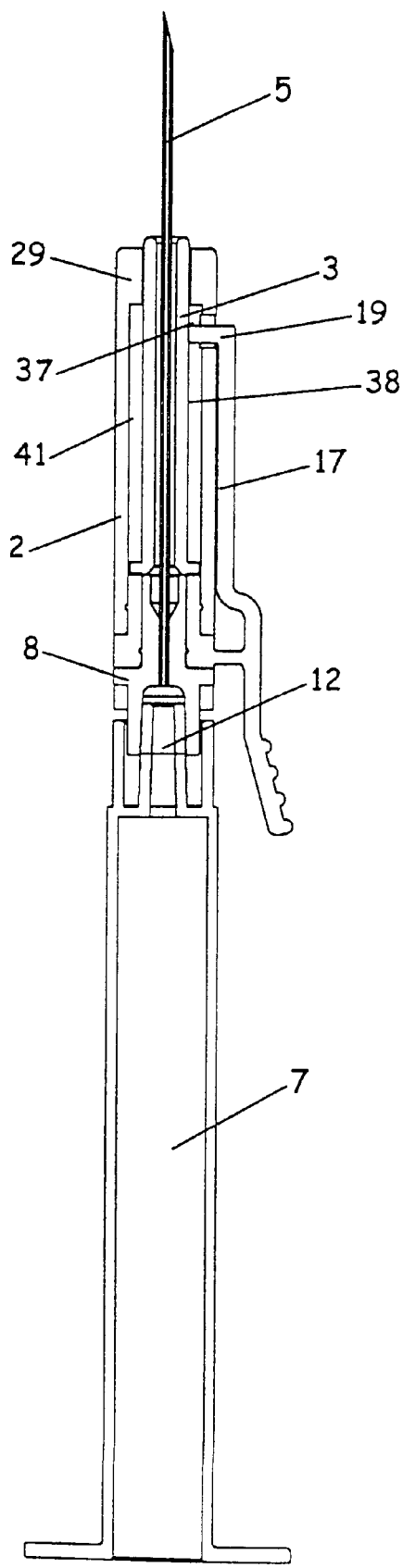
FIG. 6B is a cross sectional view of the needle assembly with the retractable hollow tube inside the stationary tube.

The components of the needle assembly 6, shown with a syringe body in FIG. 1, comprises from proximal to distal end, a needle hub 8, a retractable tube lock 1, a retractable hollow tube 3 and a stationary hollow tube 2. The needle hub 8, as shown in FIG. 2, 2A and 2B, is preferably cylindrical in shape with approximately half of its length, herein referred to as proximal half 9, circumferentially wider than the distal half 11. In the design shown where there is a distinct break between the two halves, the location of the break is referred to as boundary. Designs without a distinct boundary will work equally well. Each end preferably has a concavity that is interconnected by a lumen 25 of a dimension just adequate to fit the chosen size of a needle as shown in FIG. 6. The proximal edge of the needle 5 with an internal lumen 13 is flushed with the rounded edge of the concavity 12 of the proximal half, herein referred to as major concavity 12, for continuity of communication between the concavity 12 and the internal lumen 13 of the needle 5 as shown in FIG. 6. Flush as used herein means, positioned on the central top of the mid-distal edge of the concavity 12. The needle traverses from the major concavity 12 through the lumen 25 and into the distal half 11 which surrounds the proximal end of the needle. The concavity 10 on the distal half 11, herein referred to as minor concavity 10, may be filled with glue or adhesive to hold the needle firmly in the hub. In usage, the needle 5 is in fluid communication with the fluid delivery device such as a syringe body 7 whose distal end engages with the proximal end of the needle hub 8 through its major concavity 12 as shown in FIG. 6B. The proximal half 9 has close to the proximal edge of its outer surface, two opposing concentric protrusion 14 adaptable for luer lock locking with a syringe body 7, if desired. Other types of connection known in the art can be employed instead of luer lock connection. The needle hub 8 connects to the retractable tube lock 1 by engagement of a protruding circumferential ring 26 on the outer surface of the distal half 11 with a corresponding circular groove 27 on an interior surface of the retractable tube lock shown in FIG. 3A and prevents longitudinal disengagement of the hub. The hub can be connected to the retractable tube lock through other means such as simply slipping the hub snugly into an end of the retractable tube lock or by the use of male and female threadings in lieu of the matching ring and groove. Rotational movement of the hub against the retractable tube lock is prevented by slipping preferably two protrusions 15 into matching slots 16 of the retractable tube lock 1. The protrusions can be of any geometric shape as the slots but are preferably rectangular. Restraining rotational movement of the hub and consequently, the needle assembly, is important because the needle assembly turns against the syringe when it attaches to or detaches from the syringe body. The protrusions resting into the slots serve like an anchor, preventing the other components of the needle assembly from turning with the syringe body. The needle hub protrusions 15 and matching slots 16 can also have matching ring and groove on their respective abutting outer and inner surfaces 43 and 44. The latter may be used to engage the needle hub with the retractable tube lock instead of the matching circumferential ring and groove connection.

Figure 3:
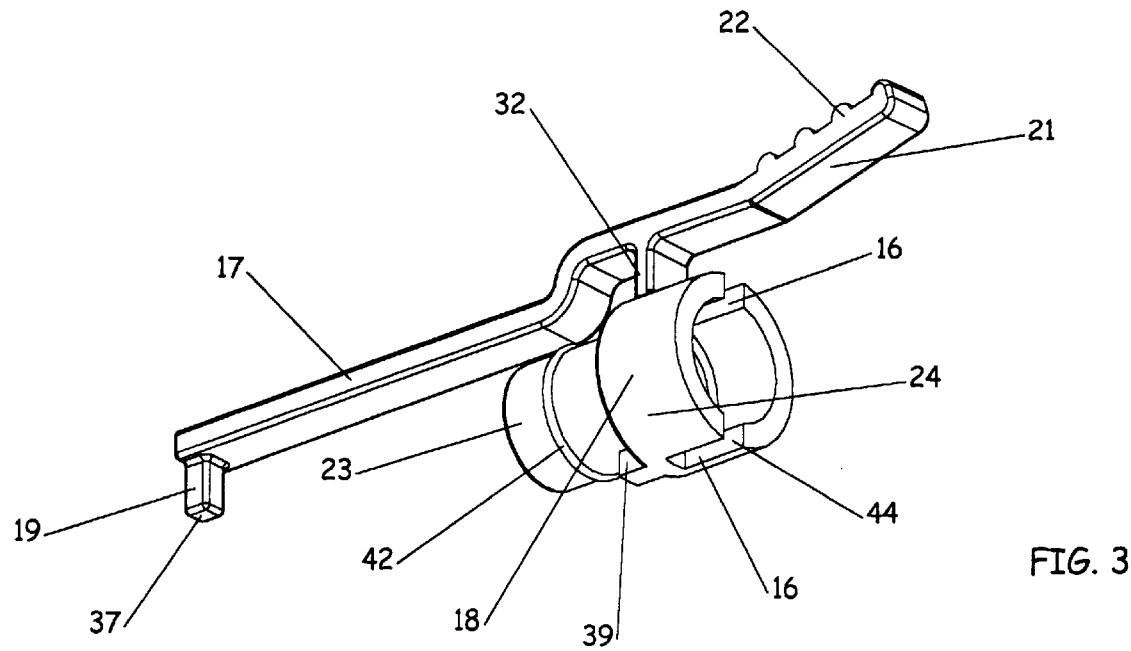
FIG. 3 is a perspective view of the retractable tube lock.
Figure 3A:
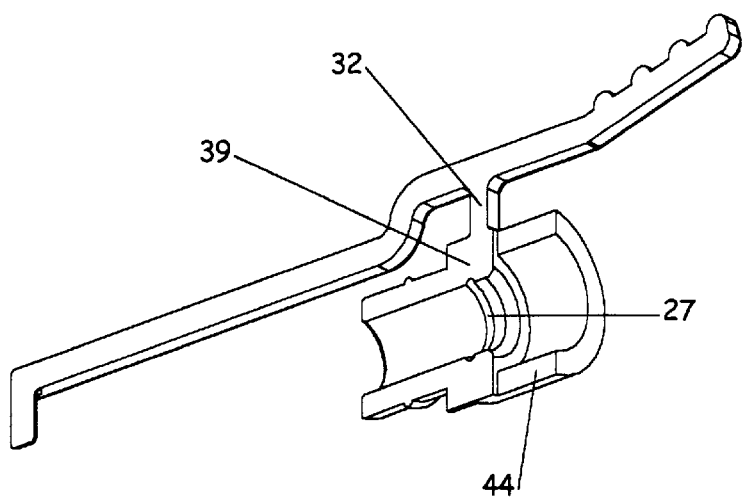
FIG. 3A is a cross sectional view of the retractable tube lock taken along B—B.
Figure 4:
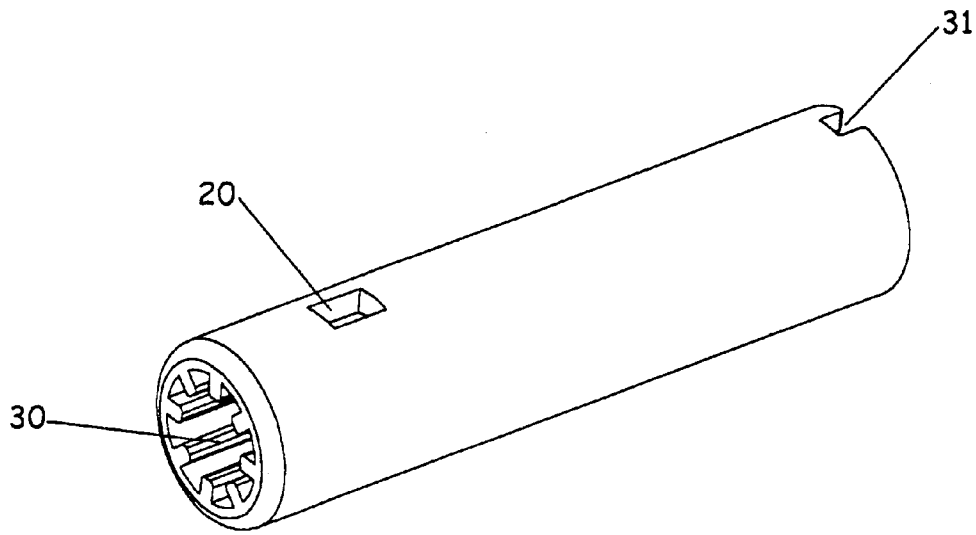
FIG. 4 is a perspective view of the stationary hollow tube.
Figure 4A:
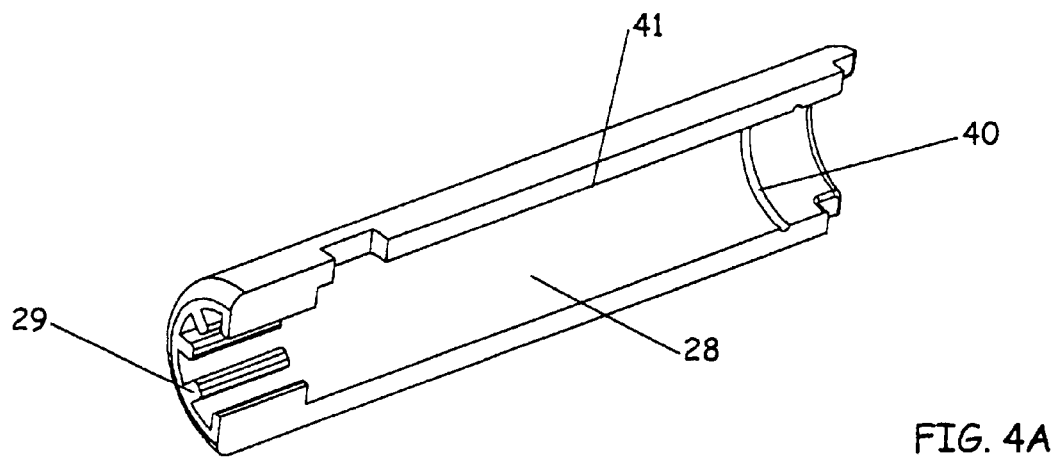
FIG. 4A is a cross sectional view of the stationary hollow tube.
Figure 5:
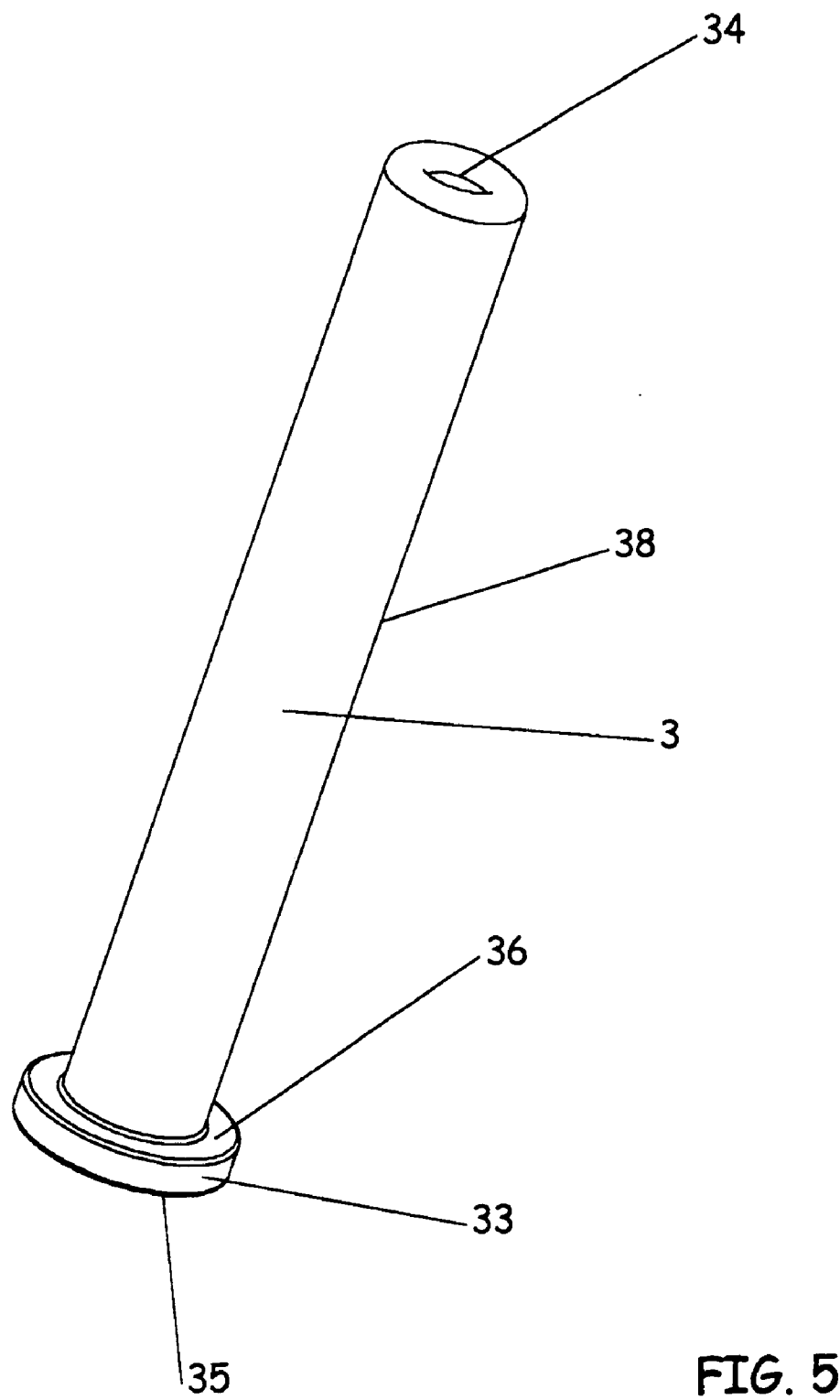
FIG. 5 is a perspective view of the retractable hollow tube.

The retractable tube lock 1 comprising an actuating latch 17 and a collar connector 18 are connected together by a joint 32 as shown in FIG. 3, which are preferably injection molded as a single piece of solid material. The joint 32 is preferably a solid material, of a kind that has some degree of flexibility and is non-brittle, durable and resilient with memory. Resilient with memory means the material will return to its original configuration when a restraining means is released. Polycarbonate is an example but other plastic compositions having said characteristics will work equally well. Although these type of materials are recommended for the joint 32, the actuating latch 17 and the whole retractable tube lock 1 is consequently made of the same material because of the limitations of the present injection molding processes. The actuating latch is an elongated bar, preferably rectangular in shape, with a step like curvature to put the plane of the distal end, closer to the stationary tube than its proximal end as shown in FIGS. 3, 6 and 6A. On the distal end of the actuating latch 17 is a locking projection 19, an inwardly directed projection that fits into a matching opening 20 at the distal end of the stationary hollow tube 2. FIG. 4 shows a perspective view of the stationary tube. During the assembly of the needle shield, the retractable tube is inserted inside the stationary tube. The projection is preferably shown herein as rectangular but other geometric shapes will work equally well. When the retractable hollow tube 3 is entirely housed inside the stationary tube 2, the tip 37 of the locking projection contacts an outer surface of the retractable hollow tube as shown in FIG. 6B. On the proximal end of the actuating latch 17 is an activating member 21 having on its top surface, a finger pad 22 where a finger can apply pressure to release the locking projection 19 from contact with the retractable hollow tube 3 housed within the stationary hollow tube 2, without completely withdrawing the locking projection from the opening 20. The application and release of pressure applied at the finger pad correspondingly seesaws the contact of the locking projection 19 on the retractable hollow tube with the joint 32 acting as a fulcrum for the actuating latch 17. The collar connector 18 as shown in FIG. 3 has on its distal end, a hollow cylindrical compartment 23 of a diameter less than the diameter of a slotted hollow cylindrical compartment 24 at its proximal end. The slots 16 of the proximal hollow cylindrical compartment 24 are the slots through which the protrusions 15 of the needle hub 8 slips into when the needle hub connects with the retractable tube lock. Bordering the distal edge of the cylindrical compartment 24 are another opposing protrusions 39, one of which is adjacent to and forwardly located from the joint 32 as shown in FIG. 3A. These protrusions which are also preferably rectangular, slips into another matching slots 31 at the proximal edge of the stationary tube 2. The distal cylindrical hollow compartment 23 has on its outside surface, a radially directed protruding ring 42 that fits snugly with a matching circumferential groove 40 in the interior or inside surface 28 of the stationary hollow tube 2 shown in FIG. 4A. This connection works in the same manner as the needle hub's circumferential ring 26 fitting into the circumferential groove 27 in the interior or inside surface of the collar of the retractable tube lock shown in FIG. 3A. Both serve the same purpose of locking the pieces or parts of the needle assembly together and preventing their longitudinal separations.

The stationary tube 2 is hollow having an outer surface and an inner surface, the inner surface 28 having a diameter slightly greater than the outer surface diameter 38 of the retractable hollow tube 3. On its distal end, covering at least $\frac{1}{2}^{th}$ but preferably $\frac{1}{6}^{th}$ of its length, are inwardly directed protrusions 29, the tips of which defines a channel 30 having a diameter smaller than the inner surface diameter 41 of the stationary hollow tube but slightly larger than the outer surface diameter 38 of the retractable hollow tube 3 as shown in FIGS. 4, 4A, 6 and 6A. The stationary hollow tube 2 is of such length and size as to completely envelope and telescopically house the retractable hollow tube 3 when it is in the retracted position but is not long enough to cover the entire length of the needle 5 as shown in FIG. 6B. When the protruding ring 42 on the same collar connector 18 fits into the matching concentric groove 40 located in the interior surface 28 of the stationary hollow tube 2 shown in FIG. 4A, the slots 31 on the stationary hollow tube that are preferably but not necessarily aligned with the opening 20, accommodates the protrusions 39 on the collar connector 18 of the retractable tube lock 1.

The needle 5 positioned into the lumen 34 of the retractable hollow tube is covered when the retractable hollow tube 3 is in its full extended position as shown in FIG. 6. For a cylindrical needle assembly, the assembly utilizes a retractable hollow tube 3 that has an outer or outside surface diameter smaller than the inner surface diameter 41 and the channel diameter 30 near the distal end of the stationary hollow tube shown in FIG. 4A and 6, to minimize friction between the sliding surfaces and allow the retractable hollow tube 3 in an axial motion, to freely slip telescopically in and out of the stationary hollow tube. The length of the retractable hollow tube is adjusted to sufficiently cover the entire length of the needle with a little more over the tip, sufficient to recess the tip of the needle inside the retractable hollow tube 3 to avoid contact by the user as shown in FIG. 6. A concentric lip 33 located on the proximal edge of the retractable hollow tube, having a diameter slightly less than the inner surface 41 of the stationary hollow tube, prevents the retractable hollow tube from completely slipping away from the stationary hollow tube 2 because the lip 33 has an outer surface diameter greater than the diameter of the channel 30 formed by protrusions 29 on the distal end of the stationary tube as shown in FIG. 6. The outer surface diameter of the concentric lip is slightly less than the interior surface diameter 41 of the stationary hollow tube located below the inwardly directed protrusions 29. The concentric lip 33 has a top 36 and a bottom 35 surface. The retractable hollow tube covers the needle 5 when it slides out of the stationary hollow tube 2. This is done by holding the needle assembly downward with the needle pointed down and releasing the contact or disengaging the locking projection 19 from the retractable hollow tube 3 by pressing on the finger pad 22 of the actuating member 21, thereby allowing the retractable hollow tube to fall freely by gravity to its full extended position. The retractable hollow tube is in its full extended position when the concentric lip 33 urges on the proximal edge of the protrusion 29 of the stationary hollow tube. It is retained in this extended position by the locking projection 19 of the retractable tube lock 1 abutting at the bottom surface 35 of the lip 33, keeping the upper surface 36 of the lip urging on the protrusion 29 as shown in FIG. 6. To uncover the needle 5, the needle assembly is held upright, then pressure is applied on the finger pad 22 of the actuating member 21 which retracts the locking projection 19 to a position where it no longer contacts the retractable hollow tube thereby allowing the retractable tube to drop inside the stationary hollow tube by gravity. The needle is kept uncovered by releasing the pressure from the finger pad after the retractable tube is inside the stationary hollow tube which allows the locking projection to again protrude through the interior of the stationary tube and rest on an outer side surface 38 of the retractable hollow tube thereby frictionally restraining its motion as shown in FIG. 6B. The above to and fro motion of the locking projection is made possible by the material make up of the actuating latch as stated above.

The safety needle assembly, is preferably constructed of a plastic material. However, glass, metal, rigid rubber copolymers and combinations of these can be used. Use of these alternate materials for the actuating latch, however, is limited by their ability to meet the requirements of flexibility, durability, non-brittleness and resiliency with memory. The needle assembly can come in a variety of sizes. The thickness of the material from which the different parts or components are made is at the discretion of the user so long as the assembly and spatial requirements disclosed above are met. FIG. 6B shows the spatial relationship of the different components of the needle assembly when the retractable tube is inside the stationary tube. FIG. 6A shows the interconnection of the components. The hub connects to the retractable tube lock through the engagement of the protruding circumferential ring 26 with the corresponding groove 27 of the retractable tube lock. The retractable tube lock in turn connects with the stationary tube housing the retractable hollow tube by the engagement of the protruding circumferential ring 42 of the retractable tube lock with the corresponding groove 40 on the interior surface of the stationary tube. The above connections are reinforced by the respective protrusions slipping into their matching slots.

A method for using the needle assembly of this invention for covering and uncovering a needle or cannula comprises the steps of releasing the locking projection of the retractable tube lock from contact with a proximal edge of the retractable hollow tube while the needle assembly is in an upright position, thereby dropping the retractable hollow tube into the stationary tube to uncover the needle or cannula for use; recontacting the locking projection with a side surface of the retractable tube to keep the needle uncovered; releasing the locking projection from contact with the retractable hollow tube after usage; inverting the needle assembly in such position as to freely drop the retractable hollow tube from the stationary hollow tube, by gravity, thereby covering the needle; and keeping the needle covered prior to discard by recontacting the proximal edge of the retractable hollow tube with the locking projection. These steps may be repeated for covering and uncovering the needle or cannula as desired.

While described herein are the currently preferred embodiments of the invention, those skilled in the art will recognize that other and further modifications may be made without departing from the invention and it is intended to claim all modifications and variations as falling within the scope of the invention.

I claim:

1. A needle assembly engageable to a fluid delivery device, comprising:
   a hub holding a needle, the hub having a hollow interior for communicating a central lumen of the needle with the fluid delivery device;
   a retractable tube lock attachable to the hub, the retractable tube lock having a distal locking projection on an actuating latch communicating with an opening of a stationary tube, the stationary tube having a hollow interior housing a retractable hollow tube, the retractable hollow tube axially movable from an extended position to cover the needle, to a retracted position to expose the needle, the movement controlled by engagement and disengagement of the distal locking projection of the retractable tube lock with the retractable hollow tube.

2. The needle assembly of claim 1 wherein the assembly has an outer surface of varying geometric shapes.

3. The needle assembly of claim 1 wherein components of the assembly are made of materials from the group consisting of plastic, glass, metal, hard rubber copolymer and combination of these.

4. The needle assembly of claim 1 wherein the actuating latch of the retractable tube lock is made of a material that is solid, non-brittle, durable and resilient with memory.

5. The needle assembly of claim 1 wherein the needle hub is cylindrical with approximately half of its length circumferentially wider than the other half.

6. The needle assembly of claim 5 further comprising a protrusion on an outer surface of the hub for engagement with a slot of the retractable tube lock.

7. The needle assembly of claim 5 further comprising a circumferential ring on an outer surface of the hub for engaging into a circumferential groove at an interior surface of the retractable tube lock.

8. The needle assembly of claim 1 wherein the stationary tube is hollow having an outer and an inner surface diameter, the inner surface diameter greater than an outer surface diameter of the retractable hollow tube to allow the retractable hollow tube to telescopically slip in and out of the stationary tube.

9. The needle assembly of claim 8 wherein on a portion of a distal end of the stationary tube are inwardly directed protrusions defining a channel having a diameter smaller than the inner surface diameter of the stationary tube but slightly larger than the outer surface diameter of the retractable hollow tube except for an outer surface diameter of a concentric lip on a proximal edge of the retractable hollow tube.

10. The needle assembly of claim 1 wherein the retractable tube lock further comprises a collar connector.

11. The needle assembly of claim 10 wherein the actuating latch and the collar connector of the retractable tube lock are connected by a joint.

12. The needle assembly of claim 10 wherein the collar connector has a distal hollow compartment and a proximal slotted hollow compartment for engagement with the needle hub.

13. The needle assembly of claim 12 wherein the distal hollow compartment have on its outer surface, a radially directed protruding ring for engagement with a matching circumferential groove on an inner surface of the stationary tube.

14. The needle assembly of claim 1 wherein the actuating latch is an elongated bar having a step like curvature to put a distal end of the actuating latch closer to the stationary tube than a proximal end, the proximal end having an activating member for applying and releasing pressure to and from the retractable tube lock.

15. The needle assembly of claim 1 wherein the retractable hollow tube has a concentric lip on its proximal edge to prevent the retractable tube from slipping away from the stationary tube.

16. The needle assembly of claim 1 wherein a cannula is held by the hub instead of a needle.

17. A method for covering and uncovering a needle or a cannula using a needle assembly having a retractable tube lock that engages and disengages a retractable hollow tube housed within a stationary tube, comprising:

(a) releasing a locking projection of the retractable tube lock from contact with a proximal edge of the retractable hollow tube while the needle assembly is in an upright position to uncover the needle or cannula;

(b) recontacting the locking projection with a side surface of the retractable tube to keep the needle or cannula uncovered;

(c) releasing the locking projection from contact with the retractable hollow tube after usage;

(d) inverting the needle assembly in such position as to freely drop the retractable hollow tube from the stationary hollow tube, by gravity, thereby covering the needle or cannula; and (d) keeping the needle or cannula covered prior to discard by recontacting the proximal edge of the retractable hollow tube with the locking projection.

18. The method of claim 17 wherein a step or steps for covering and uncovering the needle or cannula is repeated according to usage.

* * * * *